(12) United States Patent
Chauveau et al.

(10) Patent No.: US 6,326,401 B1
(45) Date of Patent: Dec. 4, 2001

(54) FORMULATION FOR THE OROMUCOSAL, IN PARTICULAR PERNASAL, ROUTE

(75) Inventors: Jacques Chauveau; Pascal Meyer; Jacques Barbet; Michel Delaage, all of Marseilles (FR)

(73) Assignee: Immunotech, Marseilles (FR)

( * ) Notice: Subject to any disclaimer, the term of this patent is extended or adjusted under 35 U.S.C. 154(b) by 0 days.

(21) Appl. No.: 09/225,742

(22) Filed: Jan. 6, 1999

(30) Foreign Application Priority Data

Jan. 15, 1998 (FR) .................................................. 98 00574

(51) Int. Cl.⁷ ..................................................... A61K 31/22
(52) U.S. Cl. ............................................ 514/547; 514/966

(58) Field of Search .................................. 514/2, 9, 966, 514/547

(56) References Cited

FOREIGN PATENT DOCUMENTS

| 0 457 701 | 11/1991 | (EP) . |
| WO 94/08622 | 4/1994 | (WO) . |

*Primary Examiner*—Zohreh Fay
(74) *Attorney, Agent, or Firm*—Browdy and Neimark

(57) ABSTRACT

A liquid pharmaceutical formulation for administration by the oro-mucosal route, comprising at least one non-polypeptidic active substance and less than 5% W/W of capryl caproyl macrogol glycerides, process for its preparation and it uses.

20 Claims, 1 Drawing Sheet

FORMULATION FOR THE OROMUCOSAL, IN PARTICULAR PERNASAL, ROUTE

FIELD OF THE INVENTION

The present invention relates to a new formulation for the oromucosal, in particular the pernasal, route.

BACKGROUND OF THE INVENTION

The oral administration route for medicamentous active substances, in particular solid active substances, is by far the most widely used. In fact, solid forms administered by the oral route are particularly suitable for ambulatory treatment, and this type of formulation usually offers a good stability with respect to time. However, this administration route, in which the active substance is administered by the buccal route, to be delivered into the stomach and the small intestine, has its limits, in particular because a large number of active substances are degraded in the gastrointestinal tract. As a result, it is often necessary to administer to the patient a dose of active substance which is considerably higher than the dose actually necessary for the activity of the product such as can be obtained by parenteral, intravenous, subcutaneous or intramuscular administration, for example, which leads to an increase in the volume of active substance to be administered. It is therefore necessary to manufacture considerably more active substance that is actually necessary in theory to obtain the desired therapeutic effect.

For this reason, new pharmaceutical forms are still being sought, in particular for active substances which are degraded particularly in the gastrointestinal tract.

Alternatives to parenteral administration, which involves sterile equipment and also aseptic conditions during the administration, which limits commercial distribution, are also still being sought.

Among the formulations suitable for ambulatory use, formulations for administration via the intermediary of the bucco-pharyngeal or nasal mucosa are also well known.

The formulations for the nasal route are generally intended for treatment of conditions of the nasal and rhinopharyngeal mucosa, and are thus essentially reserved for local treatment. This pharmaceutical form is rarely used for more general uses.

The formulations for the buccal route are generally intended for local treatment of conditions of the buccal mucosa, such as aphthae. This pharmaceutical form is also rarely used for systemic uses.

It would thus be desirable to have available an effective pharmaceutical formulation which is particularly suitable for ambulatory treatment, in particular suitable for medicaments which have a tendency to be degraded particularly by oral administration. Such a pharmaceutical formulation should cause neither irritation nor lesion of the mucosa.

Practice in the pharmaceuticals industry demands a large number of quality controls, and it would also be desirable if the nature of such a formulation is such that it does not interfere with direct assay of the active substance, such that it is easy to follow the product in a manufacturing chain or to identify the product. The phase of extraction of the active substance for its characterization would thus be avoided.

It would also be desirable to administer significant doses of active substances in volumes which are as reduced as possible.

In the majority of pathologies, it is desirable to obtain the fastest possible effect. For this reason, a particularly advantageous pharmaceutical formulation would be capable of achieving the fastest possible medicamentous effect, in addition with a good reproducibility of the administration.

SUMMARY OF THE INVENTION

The Applicant has now discovered, surprisingly, that particular pharmaceutical formulations for the oro-mucosal route, in particular for the nasal route, are a solution which is particularly suitable for the problems described above.

The present invention thus relates to a liquid pharmaceutical formulation for administration by the oro-mucosal, in particular nasal, route, characterized in that it comprises at least one non-polypeptidic active substance and less than 5% W/W of capryl caproyl macrogol glycerides (sometimes referred to as $C_8$–$C_{10}$ saturated polyglycolysated glycerides).

WO-A-94/08622 discloses pharmaceutical formulations comprising an active substance and saturated or unsaturated polyglycolysed glyceride, but the active substance is a polypeptide of about 32 amino acids, particularly calcitonin, and the saturated or unsaturated polyglycolysed glycerides represents 7% or more, generally 35 to 90% by weight and more of the formulation which usually is a gel or is solid. Whenever these formulations comprise caproyl macrogol glycerides such as Labrasol, such compounds represent 20% or more of the formulation.

In the present invention and hereafter, "oro-mucosal route" is understood as meaning the mucosa lining the buccal, nasal or pharyngeal cavities.

"Polypeptidic active substance" is understood as meaning an active substance comprising a chain of at least 10 amino acids.

The administration of an active substance by the oromucosal route can involve administration of an effective dose of active substance in the form of a single dose or fractionated doses.

The active substance can be of any nature with the above proviso, and there may be mentioned, for example, antibiotics, bacteriostatics, antihistamines, analgesics and medicaments for cardioangiology, such as antihypertensives, diuretics, vasodilators and vasoconstrictors. The active substance can also be for endocrinology, and in this respect there may be mentioned oestrogens, oestroprogestogens, glucocorticoids, hypothalamic or hypophysial hormones or progestogens. It can also be an active substance for infectiology, such as antibiotics or antibacterial agents, antiviral agents or vaccines. It can also be a compound for neurology, such as analgesics.

The active substance can be, in particular, a compound derived from an endogenous mediator, in particular one of those described in EP-A-0 457 701, that is to say a derivative of biologically active molecules containing a primary amine function and a hydroxylated nucleus or one of their addition salts with mineral or organic acids, of the formula (I):

$$[R'R''N\text{—}A\text{—}B\text{—}O\text{—}CH_2\text{—}CO]_nR_1 \qquad (I)$$

or of the formula (II)

$$R'R''N\text{—}A\text{—}B\text{—}O\text{—}CH_2\text{—}CO\text{—}NH\text{—}R\text{—}NH\text{—}CO\text{—}CH_2\text{—}O\text{—}B\text{—}A\text{—}NR'R'' \qquad (II)$$

in which n represents an integer from 1 to 10; A represents a linear or branched alkylene chain containing 1 to 5 carbon atoms; B represents an aromatic nucleus containing 6 to 10 optionally substituted carbon atoms and optionally a heteroatom; $R_1$ represents an amino radical or an alcohol radical chosen from phenols, which are optionally substituted, and aliphatic $C_1$–$C_{16}$ alcohols; R' and R" represent an alkyl radical containing 1 to 5 carbon atoms or a hydrogen atom and R represents a divalent diamine or polyamine radical, in particular the derivatives mentioned as preferred in this patent, and especially tryptamine 5-O-carboxymethyl-tyrosyl-glycinamide (IS 159), called "IS 159" below, or one of its salts.

The active substance can also be, in particular, an antimigraine active substance, such as a triptan, such as sumatriptan or zolmitriptan.

The active substance may represent important amounts in the formulation, up to the limit of solubility of the active substance in the said formulation.

The capryl caproyl macrogol glycerides are also known by the name of saturated polyglycosylated $C_8$–$C_{10}$ glycerides. Some of them are marketed by the company GATTEFOSSE under the name Labrasol®.

Capryl caproyl macrogol glycerides are mixtures of monoesters, diesters and triesters of glycerol and monoesters and diesters of macrogol with an average molecular weight of between 200 and 400.

These compounds can also be obtained by partial alcoholysis of medium-chain triglycerides using macrogol, or by esterification of glycerol and macrogol with caprylic acid and capric acid or of a mixture of esters of glycerol and an ethylene oxide condensate with caprylic acid and capric acid.

In preferred embodiments of the invention, less than 3% weight/weight of capryl caproyl macrogol glycerides is used in a finished pharmaceutical formulation, preferably 0.5 to 2.5%, and especially 1.5 to 2.2%.

In other preferred embodiments of the invention, the above formulation also comprises at least one preservative. The preservative which can be used is any preservative suitable for achieving a homogeneous formulation, and especially an alkali metal benzoate, in particular sodium benzoate. The use of sodium benzoate as the preservative gives particularly interesting results. In fact, for example by using benzoic acid or methyl and propyl parahydroxybenzoate, an instability of the mixture is observed, manifesting itself, for example, by flocculation or by phase separation.

The preservative can be present in the proportions indicated in the various pharmacopoeias, and in particular in proportions ranging from 0.05% to 1.5% by weight for the benzoates, expressed as benzoic acid, in particular 0.1 to 0.3% by weight, and in particular about 0.2% by weight in a finished pharmaceutical formulation.

In other preferred embodiments of the invention, the above formulation also comprises an isotonicity agent which is well known in the prior art, and in particular sodium chloride.

In the case where sodium chloride is used, its proportion is advantageously about 9 parts per thousand by weight in a finished pharmaceutical formulation.

In still further preferred embodiments of the invention, the above formulation is a liquid nasal formulation, characterized in that it has a pH of between 4 and 9, in particular between 5 and 8.

In still further preferred embodiments of the invention, the above liquid nasal formulation comprises 5 to 100 mg/ml of an above active substance. A unit dose will be, for example, 0.1 to 20 mg of an active substance.

The final volume of a liquid formulation according to the invention is advantageously adjusted with the aid of water for injectable preparations.

The active substance is preferably dissolved in the formulation.

Other excipients usually employed in these pharmaceutical formulations of this type, such as aqueous vehicles, emulsifiers and non-aqueous vehicles, can also be incorporated into the formulations according to the invention.

The present invention also relates to an above liquid pharmaceutical formulation, characterized in that it comprises, in aqueous solution or in the presence of a pharmaceutically acceptable solvent, tryptamine 5-O-carboxymethyl-tyrosyl-glycinamide (IS 159), or of one of its salts, in a dose which is effective for the pernasal route, and in that it has a pH of 4 to 8, in particular 6 to 7.

The present invention also relates to an above liquid pharmaceutical formulation, characterized in that it has a concentration of 5 to 100 mg tryptamine 5-O-carboxymethyl-tyrosyl-glycinamide per ml, and in that a unit dose comprises between 0.1 and 20 mg tryptamine 5-O-carboxymethyl-tyrosyl-glycinamide.

The present invention also relates in particular to an above liquid pharmaceutical formulation for administration by the nasal route, comprising about 4 g tryptamine 5-O-carboxymethyl-tyrosyl-glycinamide (IS 159), 0.9 g NaCl, 2 g Labrasol®. 0.1175 g sodium benzoate, and water for an injectable preparation qsp 100 g, the final pH being between pH 6 and pH 7.

The present invention also relates to a process for the preparation of a formulation described above, characterized in that the active substance or substances is or are mixed with capryl caproyl macrogol glycerides and with the other desired pharmaceutically acceptable excipients by methods which are known per se.

The formulations according to the invention have remarkable properties.

Firstly, as regards the bioavailability of the active substance, and taking the subcutaneous route as the reference route (100%), during tests carried out, whereas by administration of an equal amount of active substance by the oral route only 1 to 5% of the effect obtained by the subcutaneous route is obtained, about 10% of the effect obtained by the subcutaneous route is obtained by the sublingual route, and better still an effect equal to about 50% of the effect obtained by the subcutaneous route is obtained by the nasal route.

In addition, the effect was obtained faster by the nasal route than by the subcutaneous route.

Furthermore, the formulations according to the invention offer the possibility of administration of significant doses of active substance in small volumes.

Moreover, an excellent reproducibility of the effect obtained between different individuals is observed by using a formulation according to the invention.

In addition, by using a formulation according to the invention, it is found that after nasal administration this does not have the tendency to run, which also achieves good comfort to the user, avoiding him having to wipe his nose, or indeed becoming irritated.

Moreover, it is possible to carry out an assay of the active substance directly in the formulation according to the invention, without having the need to extract it. This characterization and assay can be carried out, in particular, by high performance liquid chromatography (HPLC) and by ultraviolet spectrometry.

The packaged formulations of the invention can be in the conventional forms used for nasal formulations, that is to say, in particular, nebulizers, predosed or non-predosed sprays, dropper bottles, multidose bottles or monodose bottles.

The present application also relates to the use of a capryl caproyl macrogol glyceride in an amount of less than 5% in a liquid pharmaceutical formulation for administration by the oro-mucosal route.

The present application also relates to a method for administration by the oro-mucosal route of at least one active substance, characterized in that the active substance or substances is or are mixed with capryl caproyl macrogol glycerides and with the other desired pharmaceutically acceptable excipients by methods which are known per se and the pharmaceutical formulation obtained in then administered, preferably on to the nasal mucosa.

Finally, the present application relates to:

The use of a capryl caproyl macrogol glyceride to increase the solubility of a product.

The use of a capryl caproyl macrogol glyceride to increase the absorption of an active substance into the blood.

The use of a capryl caproyl macrogol glyceride to increase the rate of absorption of an active substance into the blood.

The use of a capryl caproyl macrogol glyceride to increase the bioavailability of an active substance.

The use of a capryl caproyl macrogol glyceride in a liquid formulation to limit the loss of active substance due to running out of the said liquid formulation.

The use of a capryl caproyl macrogol glyceride in a formulation to ensure a better reproducibility of the nasal administration.

A method for treatment of a human suffering from or subject to migraines, which comprises the administration of an above formulation in which the active substance is a antimigraine agent, in particular by the pernasal route.

The example which follow illustrate the present invention.

Example 1

Formulation Examples a) Solution for nasal administration 0.9 g sodium chloride and 0.235 g sodium benzoate are introduced into 94.67 g water for injectable preparations. The mixture is stirred until dissolution is complete. 2 g Labrasol® are then introduced, while stirring slowly. 4 g IS 159 are then added until dissolution is complete. The solution is then filtered over 0.22 µm cellulose acetate.

The aqueous solution obtained is then divided among nebulizer bottles.

b) Control solution

As the control solution, preparations in which the Labrasol® was replaced by 2 ml distilled water were also prepared.

c) Sublingual tablets

A formulation having the following composition was prepared:

| | |
|---|---|
| IS 59 | 10 mg |
| Labrasol ® | 2 mg |

Other excipients: lactose, microcrystalline cellulose, pregelatinized maize starch, colloidal silica, magnesium stearate.

Example 2

Assay of the Active Substance in the Presence of Labrasol® By UV-Visible Spectrophotometry The solution of example 1 is diluted 1/800 in distilled water. The absorbances measured at 280 nm and at 350 nm are identical to those obtained in the absence of Labrasol®.

The use of Labrasol® therefore does not interfere with the assay of the active substance by UV-visible spectrophotometry.

Example 3

Assay and Analysis of the Active Substance in the Present of Labrasol® By HPLC

The solution of example 1 is diluted 1/200 by the isocratic eluent made up of 90 volumes of triethylaminephosphoric acid (TPA) pH 2.5 and 10 volumes of acetonitrile (ACN) and is analysed by HPLC (high performance liquid chromatography) at 210 nm.

Figure 1:
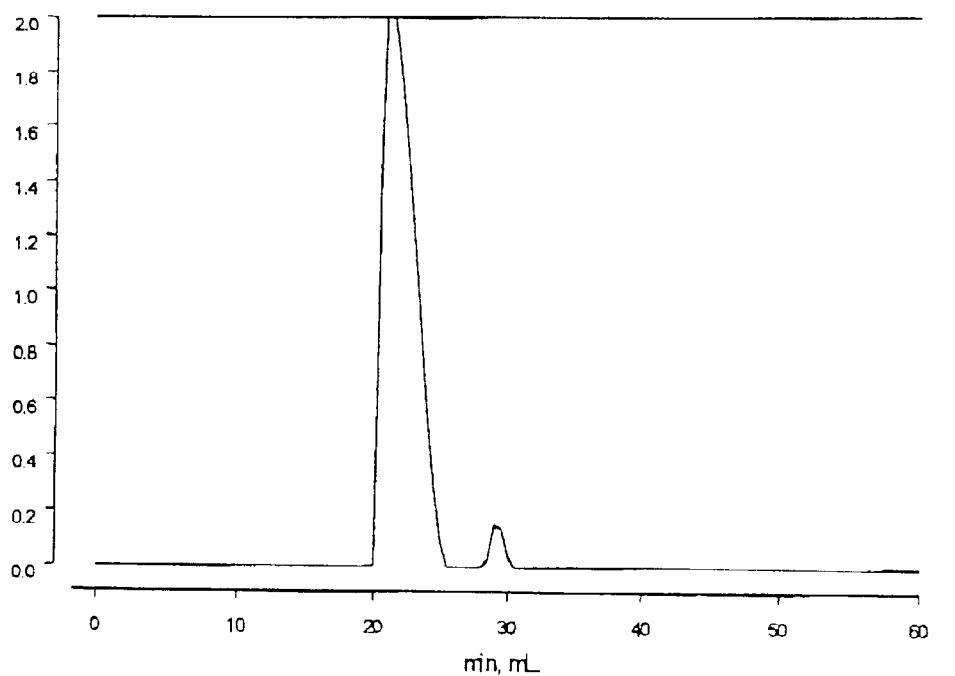
FIG. 1 shows the result of HPLC analysis of the solution of example 1 under the conditions specified in this example.

FIG. 1 shows the result of the analysis. The scale on the abscissa represents the elution parameters expressed in min (or ml, since the flow rate is 1 ml/min) and the scale on the ordinate represents the absorbance.

The same procedure is followed with the control solution. The profile of the high performance liquid chromatography and the height of the peaks are identical in the two cases.

The use of Labrasol® thus does not change the criteria of direct analysis of the active substance and the preservative by the HPLC method.

Example 4

Bioavailability Test

After nasal administration in man of an equal volume of the solution and control solution of example 1, the serum concentrations of IS 159 were measured as a function of time.

The presence of Labrasol® increases the absorption (Cmax) of IS 159 and reduces the delay in the appearance of IS 159 in the serum (apparent Tmax observed: control 30 min, with Labrasol® 10 to 15 min).

The use of Labrasol® considerably increases the bioavailability of IS 159 by the nasal route, evaluated by the area under the curve (AUC) of the concentration of IS 159 as a function of the time which elapses for an observation period of 4 hours, from 12 to 85 ng/ml/h.

Example 5

Reproducibility of the Compared Bioavailability of the Aqueous Nasal Solution Plus Labrasol®

The serum concentration of IS 159 as a function of time were measured on a group of 8 subjects after nasal administration of an identical amount of 100 µl (that is to say 4 mg active substance IS 159) of the solution of example 1.

The interindividual and intraindividual reproducibilities of the pharmacokinetic parameters of IS 159 in aqueous nasal solution in the presence of Labrasol® prove to be good.

The serum concentrations of IS 159 as a function of time were also measured on a group of 8 subjects after nasal administration of identical quantities of the solution of example 1 (4 mg active substance IS 159) during sessions separated with respect to time.

The interindividual and intraindividual reproducibilities of the pharmacokinetic parameters of the solution of example 1 prove to be equally good.

Example 6 nStudy of the Dose/Effect and Reproducibility of the Compared Bioavailability

The serum concentrations of IS 159 as a function of time were measured on the same individual after nasal administration of increasing amounts of the solution of example 1 (corresponding to 4 mg and 7 mg active substance).

The serum concentrations of IS 159 as a function of time were also measured on groups of 8 subjects after nasal administration of increasing amounts of the solution of example 1 (corresponding, for example, to 4 mg and 7 mg active substance IS 159).

Figure 2:
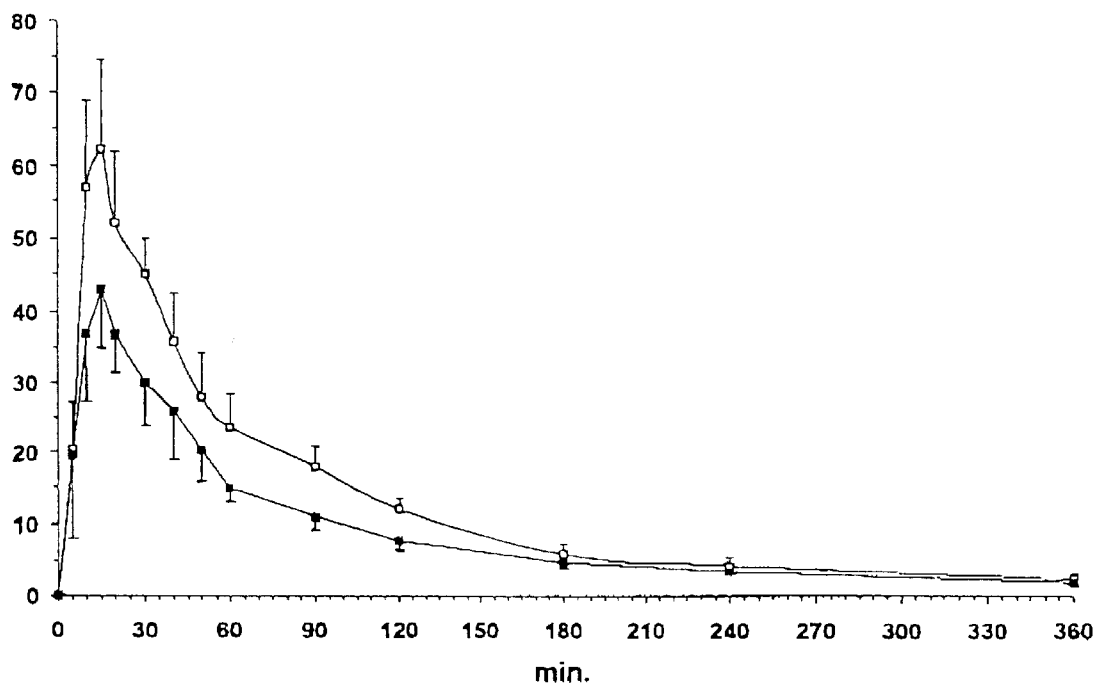
FIG. 2 shows the concentration of IS 159 as a function of time and the corresponding standard deviation.

FIG. 2 shows the concentration of IS 159 measured, expressed in ng/ml, as a function of time, expressed in minutes, and the corresponding standard deviation. The black squares represent the dose of 4 mg and the white squares represent the dose of 7 mg.

The ratios of the AUCs and the maximum concentrations obtained prove to be constant and high.

The bioavailability and absorption of this nasal formulation are found to be significant. This high absorption furthermore proves to be very fast.

The good intra-individual and interindividual reproducibility of the pharmacokinetic parameters remain preserved.

Example 7

Comparison Between Sublingual Formulations Without and With Labrasol®

IS 159 was administered by the sublingual route.

a) Assay and analysis

The supernatants of dissolution, with the aid of 1 ml distilled water, of the sublingual tablets of example 1 dosed with 10 mg IS 159 with 2% Labrasol® and of tablets without Labrasol® (2% lactose) were compared.

After dilution to 1/200 in distilled water of the dissolution supernatants, the absorbance was measured by UV-visible spectrophotometry in both cases.

The absorbances measured at 280 nm and at 350 nm prove to be identical.

Labrasol® therefore does not trap the active substance.

The use of Labrasol® does not interfere with the assay of IS 159 by UV-visible spectrophotometry, and does not interfere with the assay of the active substance contained in the tablet.

After dilution to 1/50 in the isocratic eluent made up of 90 volumes of triethylaminephosphoric acid (TPA) pH 2.5 and 10 volumes of acetonitrile (ACN), HPLC analysis of the samples was carried out.

The HPLC profile obtained on a µBondapack column is identical in the two cases.

The use of Labrasol® therefore does not change the criteria of direct analysis of the active substance by the HPLC method.

b) Compared bioavailability of sublingual formulations without and with Labrasol®

The serum concentrations of IS 159 as a function of time were measured on healthy volunteer subjects. These subjects received an identical amount of active substance IS 159 (10 mg) in the form of tablets in the absence or presence of Labrasol® (2%) by sublingual administration.

The presence of Labrasol® increases the absorption (Cmax) of IS 159 and decreases the delay in the appearance of IS 159 in the serum (apparent Tmax observed: control 45 min, with Labrasol® 35 min).

The use of Labrasol® considerably increases the bioavailability of IS 159 by the sublingual route, evaluated by the area under the curve (AUC) of the concentration of IS 159 measured as a function of time for an observation period of 6 hours, from 0.42 for the control (2% lactose) to 9.72 ng/ml/h with Labrasol®.

Example 8

Comparison Between the Aqueous Nasal Solution and the Sublingual Formulation

The serum concentrations of IS 159 as a function of time were measured on healthy volunteer subjects. The subjects received an identical amount of 10 mg IS 159 in the form of tablets with the formula indicated in example 7 comprising 2% Labrasol®, or by nasal administration of the solution of example 1.

In the presence of Labrasol® and at the same concentration of active substance, the aqueous nasal solution has a considerably better bioavailability than the corresponding sublingual formulation. The bioavailability of IS 159 by the nasal route, evaluated by the area under the curve (AUC) of the serum concentration of IS 159 evaluated from time 0 to infinity, is 166 ng/ml/h, against 12 ng/ml/h for the sublingual formulation with Labrasol®, which itself already showed a considerably better bioavailability than the sublingual formulation without Labrasol®.

The terminal half-life of IS 159 remains constant and close to 2 hours and thirty minutes.

Example 9

Compared Bioavailability of the Aqueous Nasal Solution/aqueous Subcutaneous Solution The serum concentrations of IS 159 as a function of time were measured on healthy volunteer subjects. These subjects received an identical amount of 4 mg IS 159 by the subcutaneous route (sc) or by nasal administration of the solution of example 1.

The bioavailability of the aqueous nasal solution of IS 159 comprising Labrasol® is found to be significant and faster than by the subcutaneous route.

The terminal half-life of IS 159 is not changed significantly.

The administration of the aqueous nasal solution therefore proves to be reproducible and pleasanter than the subcutaneous administration.

| | AUC/dose (h.ng/ml)(mg dose IS 159) | Cmax/dose ng/ml | Tmax in minutes | Terminal half-life |
|---|---|---|---|---|
| Mean nasal | 14 | 11 | 15 | 2.5 h |
| Mean s.c. | 36 | 20 | 30 | 2.5 h |
| Nasal/s.c. | ratio = 39% | ratio = 55% | reduced | not changed |

COMPARISON EXAMPLE

The sodium benzoate in example 1 was replaced by 0.15 g benzoic acid, 0.2 g methyl parahydroxybenzoate and 0.2 g propyl parahydroxybenzoate. In the three cases, an instability of the solution, in particular of the flocculation and phase separation type, was observed.

What is claimed is:

1. A liquid pharmaceutical formulation for administration by the oro-mucosal route, comprising at least one non-polypeptidic active substance and less than 5% W/W of capryl caproyl macrogol glycerides.

2. A liquid pharmaceutical formulation according to claim 1, for administration by the nasal route.

3. A liquid pharmaceutical formulation according to claim 1, packaged in a form used for nasal formulations, such as nebulizers, predosed or non-predosed sprays, dropper bottles or monodose or multidose bottles.

4. A liquid pharmaceutical formulation according to claims 1, comprising 3% or less weight/weight of capryl caproyl macrogol glycerides in a finished formulation.

5. A liquid pharmaceutical formulation according to claim 1, comprising from 0.5 to 2.5% weight/weight of capryl caproyl macrogol glycerides in a finished formulation.

6. A liquid pharmaceutical formulation according to claim 1, further comprising a preservative.

7. A liquid pharmaceutical formulation according to claim 1, further comprising alkali metal benzoate as a preservative.

8. A liquid pharmaceutical formulation according to claim 1, comprising a derivative of biologically active molecules containing a primary amine function and a hydroxylated nucleus or one of their addition salts with mineral or organic acids, of the formula (I):

$$[R'R''N{-}A{-}B{-}O{-}CH_2{-}CO]_n R_1 \qquad (I)$$

or of the formula (II)

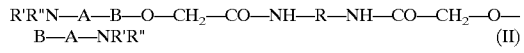

$$R'R''N{-}A{-}B{-}O{-}CH_2{-}CO{-}NH{-}R{-}NH{-}CO{-}CH_2{-}O{-}B{-}A{-}NR'R'' \qquad (II)$$

in which n represents an integer from 1 to 10; A represents a linear or branched alkylene chain containing 1 to 5 carbon atoms; B represents an aromatic nucleus containing 6 to 10 optionally substituted carbon atoms and optionally a heteroatom; $R_1$ represents an amino radical or an alcohol radical chosen from phenols, which are optionally substituted, and aliphatic $C_1$–$C_{16}$ alcohols; R' and R'' represent an alkyl radical containing 1 to 5 carbon atoms or a hydrogen atom and R represents a divalent diamine or polyamine radical.

9. A liquid pharmaceutical formulation according to claim 1, comprising, in aqueous solution or in the presence of a pharmaceutically acceptable solvent, tryptamine 5-O-carboxymethyl-tyrosyl-glycinamide (IS 159), or of one of its salts, in a dose which is effective by the pernasal route, and in that it has a pH of 4 to 8.

10. A liquid pharmaceutical formulation according to claim 9, wherein the pH of the formulation is from 6 to 7.

11. A liquid pharmaceutical formulation according to claim 9, comprising from 5 to 100 mg tryptamine 5-O-carboxymethyl-tyrosyl-glycinamide (IS 159) per ml, and wherein a unit dose comprises between 0.1 and 20 mg tryptamine 5-O-carboxymethyl-tyrosyl-glycinamide (IS 159).

12. A liquid pharmaceutical formulation according to claim 1 for administration by the nasal route, comprising about 4 g tryptamine 5-O-carboxymethyl-tyrosyl-glycinamide (IS 159), 0.9 g NaCl, 2 g Labrasol®, 0.1175 g sodium benzoate, and water for an injectable preparation qsp 100 g, the final pH being between pH 6 and pH 7.

13. A process for the preparation of a liquid pharmaceutical formulation according to claim 1, comprising mixing active substance or substances with the capryl caproyl macrogol glycerides and with the other desired pharmaceutically acceptable excipients by conventional methods.

14. A liquid pharmaceutical formulation according to claim 8, comprising 3% or less weight/weight of capryl caproyl macrogol glycerides in a finished formulation.

15. A liquid pharmaceutical formulation according to claim 14, comprising, in aqueous solution or in the presence of a pharmaceutically acceptable solvent, tryptamine 5-O-carboxymethyl-tyrosyl-glycinamide (IS 159), or of one of its salts, in a dose which is effective by the pernasal route, and in that it has a pH of 4 to 8.

16. A liquid pharmaceutical formulation according to claim 8, comprising, in aqueous solution or in the presence of a pharmaceutically acceptable solvent, tryptamine 5-O-carboxymethyl-tyrosyl-glycinamide (IS 159), or of one of its salts, in a dose which is effective by the pernasal route, and in that it has a pH of 4 to 8.

17. A liquid pharmaceutical formulation according to claim 4, comprising, in aqueous solution or in the presence of a pharmaceutically acceptable solvent, tryptamine 5-O-carboxymethyl-tyrosyl-glycinamide (IS 159), or of one of its salts, in a dose which is effective by the pernasal route, and in that it has a pH of 4 to 8.

18. A liquid pharmaceutical formulation according to claim 15, wherein the pH of the formulation is from 6 to 7.

19. A liquid pharmaceutical formulation according to claim 16, wherein the pH of the formulation is from 6 to 7.

20. A method of treatment comprising administering a liquid pharmaceutical composition in an amount of less than 5% W/W of capryl caproyl macrogol glyceride in said liquid pharmaceutical formulation by the oro-mucosal route.

* * * * *